(12) United States Patent
Larsson Mastonstråle

(10) Patent No.: US 10,280,753 B2
(45) Date of Patent: May 7, 2019

(54) FUEL PRODUCTION USING SOLAR ENERGY

(71) Applicant: SUNTHETICS AB, Finspång (SE)

(72) Inventor: Stefan Larsson Mastonstråle, Älvkarleby (SE)

(73) Assignee: SUNTHETICS AB, Finspång (SE)

(*) Notice: Subject to any disclaimer, the term of this patent is extended or adjusted under 35 U.S.C. 154(b) by 135 days.

(21) Appl. No.: 15/312,912

(22) PCT Filed: May 21, 2015

(86) PCT No.: PCT/SE2015/050586
§ 371 (c)(1),
(2) Date: Nov. 21, 2016

(87) PCT Pub. No.: WO2015/178850
PCT Pub. Date: Nov. 26, 2015

(65) Prior Publication Data
US 2017/0138196 A1  May 18, 2017

(30) Foreign Application Priority Data
May 21, 2014 (SE) ........................ 1450607

(51) Int. Cl.
C07C 29/15 (2006.01)
F01B 23/10 (2006.01)
(Continued)

(52) U.S. Cl.
CPC .............. F01B 23/10 (2013.01); C07C 29/15 (2013.01); C25B 1/003 (2013.01); C25B 1/04 (2013.01);
(Continued)

(58) Field of Classification Search
CPC . C07C 29/15; F01B 23/10; C25B 1/04; F03G 6/001
See application file for complete search history.

(56) References Cited

U.S. PATENT DOCUMENTS 4,776,171 A  10/1988 Perry et al.
5,875,635 A   3/1999 Platell
(Continued)

FOREIGN PATENT DOCUMENTS

CN  201367997 Y  * 12/2009
WO     0025380 A2    5/2000
(Continued)

OTHER PUBLICATIONS

Yujing CN201367997Y, English machine translation (Year: 2009).*
(Continued)

Primary Examiner — Susan D Leong
(74) Attorney, Agent, or Firm — RMCK Law Group, PLC

(57) ABSTRACT

There is provided a method of producing a product. The method comprises: supplying electricity generated in a photovoltaic cell arrangement and a piston engine, respectively, to electrolytic and catalytic reactions that are heated by concentrated sunlight; reacting carbon dioxide and water in the heated electrolytic and catalytic reactions to form a pressurized product, such as pressurized methanol; and expanding the pressurized product in the piston engine to generate electricity. There is also provided a system for production of the product as well as devices to be used in the method or system.

6 Claims, 5 Drawing Sheets

(51) Int. Cl.
    *C25B 1/00*     (2006.01)
    *F03G 6/00*     (2006.01)
    *C25B 1/04*     (2006.01)
    *C25B 9/00*     (2006.01)
    *H01G 9/20*     (2006.01)

(52) U.S. Cl.
    CPC ............... C25B 9/00 (2013.01); F03G 6/001 (2013.01); H01G 9/20 (2013.01); *Y02E 10/46* (2013.01); *Y02E 60/366* (2013.01); *Y02E 70/10* (2013.01); *Y02P 20/134* (2015.11)

(56) References Cited

U.S. PATENT DOCUMENTS

| | | |
|---|---|---|
| 2002/0025457 A1 | 2/2002 | Dodd et al. |
| 2002/0159929 A1* | 10/2002 | Kaneko ................ C07C 29/152 422/140 |
| 2009/0313886 A1 | 12/2009 | Hinman et al. |
| 2010/0000874 A1 | 1/2010 | Hinman et al. |
| 2011/0209476 A1* | 9/2011 | Chae ....................... F24S 20/20 60/641.15 |
| 2013/0205647 A1 | 8/2013 | McAlister |
| 2014/0238021 A1* | 8/2014 | Harif ....................... F01K 13/00 60/653 |

FOREIGN PATENT DOCUMENTS

| | | |
|---|---|---|
| WO | 2012110339 A1 | 8/2012 |
| WO | 2013105097 A1 | 7/2013 |

OTHER PUBLICATIONS

Wolfgang (WO 2012110339A1) English machine translation (Year: 2012).*
International Search Report and Written Opinion for International Application No. PCT/SE2015/050586 dated Nov. 4, 2015, 13 pages.
Pearson, Richard J., et al., "Energy Storage via Carbon-Neutral Fuels Made From CO2, Water, and Renewable Energy," Proceedings of the IEEE, vol. 100, No. 2, Feb. 2012, pp. 440-460.

* cited by examiner

FUEL PRODUCTION USING SOLAR ENERGY

CROSS-REFERENCE TO RELATED APPLICATIONS

This application is a 371 U.S. National Stage of International Application No. PCT/SE2015/050586, filed May 21, 2015, which claims priority to Swedish Application No. 1450607-5, filed on May 21, 2014. The disclosure of each of the above applications is incorporated herein by reference in their entirety.

TECHNICAL FIELD

The present invention relates to solar-assisted fuel production as well as components for use in such a production.

BACKGROUND

US2002025457 discloses a method for the storage of electrical and thermal energy or of hydrogen. The method includes the steps of electrolysis of water to yield hydrogen, reaction of the hydrogen with carbon dioxide to form methanol and storage of the methanol. The electricity may be generated by solar panels. Subsequently, the methanol is converted back to hydrogen or used to fuel an engine or generate electricity.

US2009313886 discloses a method, in which products from a solar assisted Reverse Water Gas Shift (RWGS) reaction are used in a hydrocarbon fuel synthesis process to create a liquid hydrocarbon fuel. A water splitter splits water molecules into hydrogen and oxygen via the addition of the solar energy. A chemical reactor chamber mixes solar heated carbon dioxide gas with all or just a portion of the hydrogen molecules from the water splitter in a RWGS reaction to produce resultant carbon monoxide. A hydrocarbon liquid fuel synthesis reactor receives and uses either all of the unconsumed portions of hydrogen from the RWGS or the remaining portion of the hydrogen molecules from the water splitter and the resultant carbon monoxide molecules from the RWGS in the hydrocarbon fuel synthesis process to create a liquid hydrocarbon fuel.

SUMMARY

The inventors have realized that use of solar radiation for both heating and generating electricity to reactions in which a product, such as methanol, of high pressure is formed from water and carbon dioxide can be area- and cost-efficient. However, the inventors have also realized that the solar-generated electricity may be insufficient, which means that an extra supply is needed for an electrolysis reaction that splits the water molecules.

Further, the inventors have realized that the high-pressure product cannot be expanded in a traditional gas or steam turbine on an industrial scale. This is because the product (e.g. methanol) is normally mixed with some amounts of unreacted reactants (water and CO2) and traditional turbines wear down when operating with such mixed media. In particular, the water is problematic and liquid separators are generally not sufficiently efficient. Instead, the inventors have found that a piston engine is more robust when expanding the mixed media and can be used for converting the overpressure of the product mixture to electricity. Finally, the inventors have realized that the electricity generated by means of the piston engine can provide the extra electricity supply needed for the electrolysis reaction.

In summary, the inventors have provided an energy-efficient method and system for production of a depressurized product, such as methanol, from water, carbon dioxide and sunlight.

Further, the inventors have invented components that can be used for implementing the system and carrying out the method.

Accordingly, there is provided a solar collector that can efficiently heat the electrolysis reactor and, concurrently, concentrate sunlight to photovoltaic cells for electricity generation.

Further, there is provided a semi-reflective photovoltaic cell arrangement that can form part of the solar collector and divides the sunlight into one fraction for heating and another fraction for photovoltaic electricity generation.

Also, there is provided a heatable reactor capable of absorbing the heating fraction of the sunlight and catalyse the formation of the product.

There are many benefits associated with the present disclosure. Firstly, solar energy can be considered the biggest energy resource available for human beings. Secondly, a liquid fuel such as methanol is a superior energy carrier when considering energy density and storage capability. The huge investments made in infrastructure for fossil fuel during the last 100 year can be further exploited with a liquid fuel. Thirdly, a liquid fuel produced using CO2 as a carbon source would be CO2 neutral and thus beneficial from a global warming perspective.

The academic world has been focused on so called artificial photosynthesis, which involves the production of hydrogen with water as a feed stock. Artificial photosynthesis has been expected to be more cost-efficient than electrolysis of water, which is a well know industrial process. Hydrogen is however known to be difficult to handle. The value of hydrogen as fuel is increased when it is combined with carbon and forms a liquid fuel according to the present disclosure.

The following is an itemized listing of embodiments of the present disclosure.
1. A method of producing a product, comprising:
supplying electricity generated in a photovoltaic cell arrangement and a piston engine, respectively, to electrolytic and catalytic reactions that are heated by concentrated sunlight;
reacting carbon dioxide and water in the heated electrolytic and catalytic reactions to form a pressurized product; and
expanding the pressurized product in the piston engine to generate electricity.
2. The method of item 1, wherein the piston engine is a hydraulic piston engine.
3. The method of item 1 or 2, wherein the piston engine is designed to operate at 5000-20000 rpm, such as 10000-15000 rpm.
4. The method of any one of the preceding items, wherein a liquid fraction is separated from the pressurized product before it is expanded in the piston engine.
5. The method of any one of the preceding items, wherein at least one solar collector concentrates solar radiation to the photovoltaic cell arrangement for electricity generation and to the reactions for heating.
6. The method of any one of the preceding items, wherein water supplied as a reactant to the electrolysis reaction is preheated by cooling the photovoltaic cell arrangement.

7. The method of any one of the preceding items, wherein the product is a fuel, such as a hydrocarbon fuel, such as methanol.

8. The method of any one of the preceding items, wherein the reactions is carried out at a temperature of at least 200° C., such as at least 300° C. and/or at a pressure of at least 120 bar, such as at least 170 bar.

9. A system for production of a product, such as methanol, comprising:
a solar collector;
a photovoltaic cell arrangement arranged at the solar collector such that sunlight may be concentrated to the photovoltaic cell arrangement by the solar collector;
an electrolytic and catalytic reactor for reacting water and carbon dioxide and forming a pressurized product, such as methanol, which reactor is arranged at the solar collector such that it may be heated by sunlight concentrated to it;
a piston engine connected to a generator arranged to expand pressurized product from the reactor and generate electricity;
an electrical connection between the photovoltaic cell arrangement and the reactor; and
an electrical connection between the generator connected to the piston engine and the reactor.

10. The system of item 11, wherein a liquid separator is arranged on a connection between the reactor and the piston engine.

11. The system of any one of items 9-10, wherein the reactor is cylinder-shaped.

12. The system of any one of items 9-11, wherein the solar collector comprises a first reflective surface generally shaped as a parabolic trough.

13. The system of item 12, wherein the reactor is arranged in a recess in the first reflective surface.

14. The system of any one of items 9-13, wherein the photovoltaic cell converts solar radiation of a first spectrum to electricity and reflects solar radiation of second spectrum to the reactor for heating.

15. The system of any one of items 9-14, wherein the piston engine is a hydraulic engine.

16. The system of item 15, wherein the hydraulic engine has 5 or 7 pistons.

17. A device for collection of sunlight comprising a first reflecting surface for primary reflection, a second reflecting surface for secondary reflection and a third reflecting surface for tertiary reflection, wherein
the first reflective surface is shaped as a parabolic trough and arranged to reflect direct sunlight,
the second reflective surface is arranged to reflect concentrated radiation from the first reflective surface, and
the third reflective surface is shaped as a parabolic trough, provided as a recess in the first surface and arranged to reflect radiation from the second reflective surface and optionally direct sunlight,
said device further comprising a heatable device, such as a tube or a reactor, arranged to receive radiation directly from the second and the third reflective surface.

18. The device of item 17, wherein a central axis of the heatable device approximately coincides with a focal line of the third reflective surface.

19. The device of item 17 or 18, wherein the parabola depth to focal length ratio of the first reflective surface is between 1:2 and 1:4, such as between 1:2.5 and 1:3.5.

20. The device of any one of items 17-19, wherein the parabola width to focal length ratio of the first reflective surface is between 2:1 and 2.6:1.

21. The device of any one of items 17-20, wherein the parabola width to focal length ratio of the third reflective surface is between 4:1 and 6:1, such as between 4.4:1 and 5.4:1.

22. The device of any one of items 17-21, wherein the parabola width of the first reflective surface is between 4 and 7 times the parabola width of the third reflective surface.

23. The device of any one of items 17-22, wherein the focal length of the first reflective surface is at least 5 times the focal length of the third reflective surface.

24. The device of any one of items 17-23, wherein parabola width of the first reflective surface is 4-8 m, such as 5-7 m, such as 5.5-6.5 m.

25. The device of any one of items 17-24, which has a length of 4-6 m, such as 4.5-5.5 m.

26. The device of any one of items 17-25, wherein the second reflective surface divides the radiation into at least four different beams of which at least two are reflected directly to the heatable device and at least two are reflected to the heatable device via the third reflective surface, such that the incident radiation is distributed around the circumferential surface of the heatable device.

27. The device of any one of items 17-26, wherein the secondary surface is semi-reflective such that a first sunlight fraction is transmitted for electricity generation in photovoltaic cells and a second sunlight fraction is reflected for heating of the heatbale device.

28. A semi-reflective photovoltaic cell arrangement comprising a plurality of non-overlapping photovoltaic cells, wherein a concave lens or lens portion having a semi-reflective surface is arranged on a first side of each photovoltaic cell such that radiation in a first wavelength range is concentrated to the photovoltaic cell and radiation of a second wavelength range is reflected and a second side of each photovoltaic cells is thermally connected to a cooling arrangement capable of cooling the photovoltaic cells.

29. The semi-reflective photovoltaic cell arrangement according to item 28, wherein the cooling arrangement comprises one or more channels for a cooling medium, such as water.

30. The semi-reflective photovoltaic cell arrangement according to item 28 or 29, wherein the cooling arrangement is composed of a metal, such as an extruded metal.

31. The semi-reflective photovoltaic cell arrangement according to any one of item 28-30, wherein the semi-reflective surface is provided by a semi-reflective surface texture or a semi-reflective layer, such as a dichromatic layer.

32. The semi-reflective photovoltaic cell arrangement according to any one of item 28-31, wherein the lenses are casted in a lens material, such as siloxane or glass, which preferably has a refractive index of 1.3-1.6, such as 1.4-1.6.

33. The semi-reflective photovoltaic cell arrangement according to item 32, wherein the photovoltaic cells lenses are embedded in the lens material.

34. The semi-reflective photovoltaic cell arrangement according to any one of items 28-33, wherein the lenses are 2D lenses.

35. The semi-reflective photovoltaic cell arrangement according to any one of items 28-34, wherein two or more aligned photovoltaic cells forming a row are covered by a common elongated 2D lens.

36. The semi-reflective photovoltaic cell arrangement according to any one of items 28-35 comprising a plurality of parallel 2D lenses each covering a row of photovoltaic cells.

37. The semi-reflective photovoltaic cell arrangement according to any one of items 28-36, wherein the lens comprises a convex top surface, a bottom surface facing the photovoltaic cell(s) and two opposed side surfaces reaching from the bottom surface to the top surface.
38. The semi-reflective photovoltaic cell arrangement according to item 37, wherein the side surfaces are reflective such that radiation transmitted through the top surface may be reflected by the side surfaces to the photovoltaic cell(s) under the bottom surface.
39. The semi-reflective photovoltaic cell arrangement according to item 37 or 38, wherein the side surfaces are leaning outwardly.
40. The semi-reflective photovoltaic cell arrangement according to any one of items 28-39, wherein the radiation in the first wavelength range comprises visible light.
41. The semi-reflective photovoltaic cell arrangement according to item 40, wherein the first wavelength range comprises 400-700 nm, 400-800 nm or 400-900 nm.
42. The semi-reflective photovoltaic cell arrangement according to any one of items 28-41, wherein the radiation in the second wavelength range comprises 1000-2000 nm, such as 900-2500 nm.
43. A reactor comprising an outer circumferential selective surface, a pipe wall provided inside the selective surface, an electrolyser layer provided inside the pipe wall, a catalytic layer provided inside the electrolyser layer and a product channel provided inside the catalytic layer.
44. The reactor of item 43, wherein the selective surface, the pipe wall and the electrolyser layer are concentric.
45. The reactor of item 43 or 44, further comprising an outer membrane or perforated tube wall provided between the electrolyser layer and the catalytic layer.
46. The reactor of any one of items 43-45, further comprising an inner membrane or perforated tube wall provided between the catalytic layer and the product channel, such that the product channel is defined by the inside of the inner membrane or perforated tube wall.
47. The reactor of any one of items 43-46, further comprising at least one oxygen valve for release of oxygen formed in the electrolyser layer.
48. The reactor of any one of items 43-47, which shaped as a cylinder.
49. The reactor of any one of items 43-48, wherein the electrolyser layer comprises electrolytic cells.
50. The reactor of any one of items 43-49, further comprising electrical connections for supply of electricity to the electrolyser layer.
51. The reactor of any one of items 43-50, wherein the catalytic layer comprises a Cu/ZnO based catalyst, optionally with added oxides, such as $Ga_2O_3$, $Al_2O_3$, $ZrO_2$ or $Cr_2O_3$.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise.

BRIEF DESCRIPTION OF THE DRAWINGS

FIG. 4a is a perspective view. FIG. 4b is a side view.

DETAILED DESCRIPTION

Figure 1:
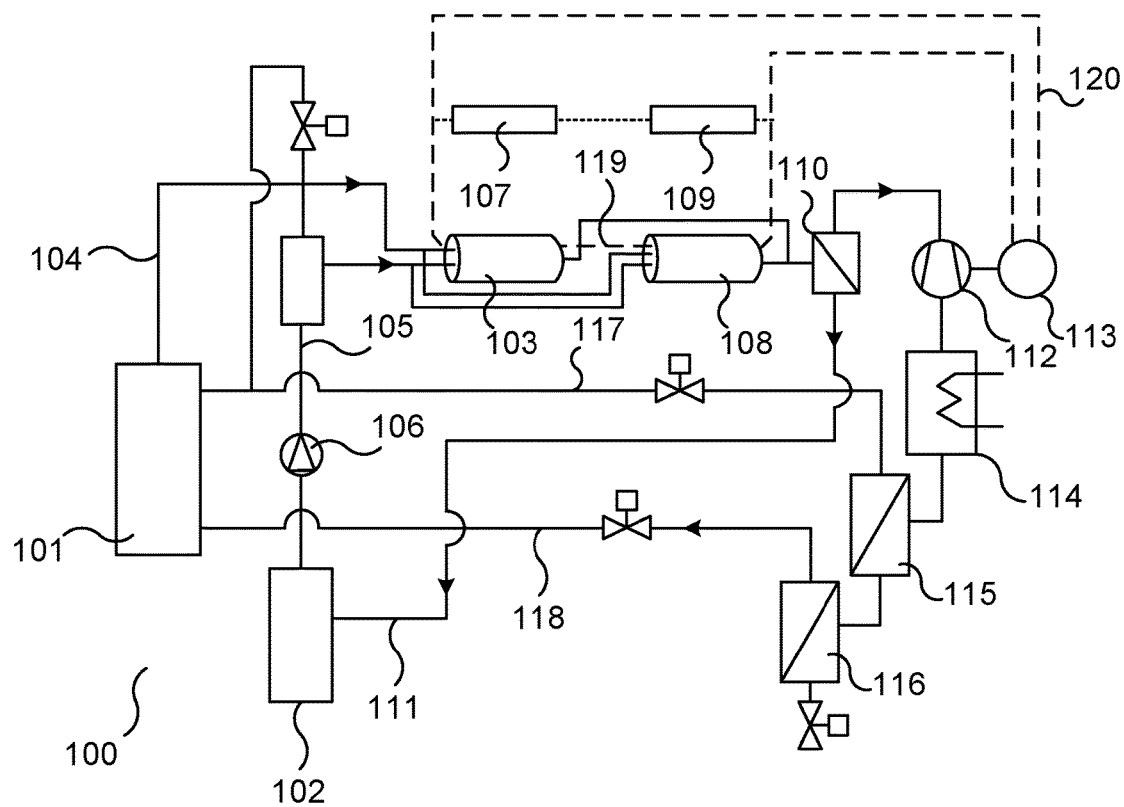
FIG. 1 illustrates an embodiment of a system according to the second aspect of the present disclosure, which can be used for carrying out the method of the first aspect of the present disclosure.

As a first aspect of the present invention, there is provided a method of producing a product. The method comprises:
supplying electricity generated in a photovoltaic cell arrangement and a piston engine, respectively, to electrolytic and catalytic reactions that are heated by concentrated sunlight;
reacting carbon dioxide and water in the heated electrolytic and catalytic reactions to form a pressurized product; and
expanding the pressurized product in the piston engine to generate electricity.

In the first aspect, water and CO2 are supplied as reactants. In the reactions, the product is formed after water electrolysis and catalytic conversion of CO2.

The reactions may for example be carried out at a temperature of at least 200° C., such as at least 300° C., such as 350-550° C. Further, the reactions may be carried out at a pressure of at least 120 bar, such as at least 170 bar, such as 170-270 bar.

Likewise, the product supplied to the piston engine may have a pressure of at least 120 bar, such as at least 170 bar, such as 170-270 bar.

Accordingly, the water and/or the CO2 may be pressurized to at least 120 bar, such as at least 170 bar, such as 170-270 bar before being supplied to the reactions.

The reactor used in the first aspect for the reactions may for example be a reactor according to the fifth aspect described below. Further, the reactor used in the first aspect may be segmented, as discussed below.

The CO2 of the present disclosure may for example be obtained from post combustion capture ("carbon capture") in power plants or other combustion processes. It may also be obtained from biogas or ethanol fermentation where it is formed as a bi-product. Further, it may be obtained from concrete production facilities, which generate substantial amounts of CO2. As another example, CO2 may be separated from sea water (e.g. by means of polymembrane separators) or air and used according to the present disclosure.

The supplied CO2 and water is normally purified to avoid contamination of the process.

In one embodiment, oxygen produced during water hydrolysis is vented from the reactions, e.g. through oxygen valves arranged in the reactor.

The product is preferably a hydrocarbon product. Further, the product is preferably a liquid at atmospheric pressure and room temperature. In a particularly preferred embodiment, the product is methanol.

The pressurized product that is expanded may be in a mixture with other components. Normally, the product mixture will comprise unreacted water and CO2. The product mixture may also comprise unreacted hydrogen gas (H2) and carbon monoxide (CO).

In the first aspect, water is hydrolysed, which requires heat and electricity. Heat is provided by concentrated sunlight and optionally from an exothermic reaction, such as a reduction consuming hydrogen produced by the electrolysis. Electricity is obtained from two different processes: i) the expansion of the pressurized product; and ii) photovoltaic conversion of sunlight.

In an embodiment of the first aspect, a first sunlight fraction is used for the photovoltaic conversion and a second sunlight fraction is used to heat the electrolytic reaction. A semi-reflective surface may be used for the division of the sunlight into the two fractions. The first fraction preferably comprises visible light and the second fraction preferably comprises comprise radiation having wavelengths above 900 nm.

The first fraction may for example comprise wavelengths of 400-800 nm, such as 400-900 nm, while the second fraction may comprise wavelengths of 1000-2000 nm, such as 900-2500 nm.

During the photovoltaic conversion, it preferred to cool the photovoltaic cells using a cooling medium. The cooling increases the efficiency of the photovoltaic cells. The cooling medium may for example be water that is then supplied to the reaction as a reactant (see above). Alternatively, heat is exchanged between the cooling medium and water supplied as a reactant. As understood by the skilled person, transfer of heat from the photovoltaic cells to the electrolytic reaction increases the overall energy-efficiency of the process.

For example, the concentrated sunlight may be provided by a device according to the third aspect described below. Further, the arrangement of the fourth aspect described below may be used for the photovoltaic conversion. When a semi-reflective surface is used for fractionizing sunlight, the semi-reflective surface may be provided by the arrangement of the fourth aspect.

The piston engine of the first aspect may for example be a hydraulic piston engine. In one embodiment, the hydraulic piston engine has 5 or 7 pistons.

Further, the piston engine may be designed to operate at 5000-20000 revolutions per minute (rpm), such as 10000-15000 rpm. Prior art turbines are normally designed to operate at 800-1500 rpm.

An example of a suitable piston engine is shown in U.S. Pat. No. 5,875,635 (see the discussion about the axial piston type engine, which has 7 cylinders and thus 7 pistons in the embodiment of FIG. 1 in U.S. Pat. No. 5,875,635).

As mentioned above, the product may be mixed with water. In one embodiment of the first aspect, water is separated from the pressurized product before it is expanded in the piston engine. Such a separation of water may reduce the wear and/or increase the efficiency in the piston engine. The separated water may be recycled for use as a reactant in the process.

As also mentioned above, the product may be mixed with CO2, CO and/or H2. In one embodiment of the first aspect, CO2, CO and/or H2 is/are separated from the product downstream the piston engine. For example, CO and/or H2 may be separated in a first separation step downstream the piston engine and CO2 may be separated in a second separation step downstream the piston engine. The separated CO2, CO and/or H2 may be recycled to the reactions as reactants.

As a second aspect of the present disclosure, there is provided a system for production of a product, comprising:
a solar collector;
a photovoltaic cell arrangement arranged at the solar collector such that sunlight may be concentrated to it by the solar collector;
electrolytic and catalytic reactor for reacting water and carbon dioxide and forming pressurized product, such as methanol, which reactor is arranged at the solar collector such that it may be heated by sunlight concentrated to it;
a piston engine connected to a generator arranged to expand pressurized product from the reactor and generate electricity;
an electrical connection between the photovoltaic cell and the reactor; and
an electrical connection between the generator and the reactor.

The system of the second aspect may be used for carrying out the method of the first aspect.

The above-mentioned embodiments of the method of the first aspect apply mutatis mutandis to the system of the second aspect. Nevertheless, some specific embodiments of the second aspect are described below.

In one embodiment of the second aspect, the reactor is cylinder-shaped. Further, the circumferential surface of the reactor may be a selective surface. A selective surface ensures efficient heat absorption.

In one embodiment, the solar collector comprises a parabolic trough. Further, the solar collector may comprise a first surface for primary reflection, a second surface for secondary reflection and a third surface for tertiary reflection. The third surface may be a recess in the first surface and the reactor may be arranged inside the recess. The recess may for example be provided with a cover such that the reactor in the recess is protected. The cover is preferably composed of a material with high transmittance. The second surface may for example be semi-reflective such that it can reflect radiation of longer wavelengths (e.g. >900 nm) to the reactor and/or third reflective surface and transmit radiation of shorter wavelengths (e.g. visible light) to the photovoltaic cell arrangement. The solar collector may thus be the device according to the third aspect described below.

The system of the second aspect preferably comprises a plurality of reactors. Such reactors may be chemically connected in parallel, which means that the product mixtures from the plurality of reactors may be routed to a common product line. Further, the reactors are preferably electrically connected in series.

Likewise, the system of the second aspect preferably comprises a plurality of photovoltaic cell arrangements. For example, each reactor may form a pair with a photovoltaic cell arrangement. Further, each such pair may be associated with a solar collector.

The above-mentioned embodiments of the system of the second aspect apply mutatis mutandis to the method of the first aspect.

As a third aspect of the present invention, there is provided a device for collection of sunlight comprising a first reflecting surface for primary reflection, a second reflecting surface for secondary reflection and a third reflecting surface for tertiary reflection.

The first reflective surface is shaped as a parabolic trough. It is also arranged to reflect direct sunlight.

The second reflective surface is arranged to reflect concentrated radiation from the first reflective surface.

The third reflective surface is provided as a recess in the first reflective surface and shaped as a parabolic trough. It is further arranged to reflect radiation from the second reflective surface. Optionally it is also arranged to reflect direct sunlight.

The device of the first aspect further comprises a heatable device, such as a tube or a reactor, arranged to receive radiation directly from the second and the third reflective surface. The heatable device is preferably shaped as a cylinder. The circumferential surface of the heatable device may for example be a selective surface for efficient heat absorption.

A surface that is shaped as parabolic trough is straight in one dimension and curved as a parabola in the other two.

In an embodiment, the second reflective surface is arranged below the focal line of the first reflective surface such that the shortest distance between second reflective surface and the focal line of the first reflective surface is less than $1/10$ of the focal length of the parabola of the first reflective surface. To be arranged "below" the focal line means to be arranged between the focal line and the vertex of the parabola of the first reflective surface.

In one embodiment, a central axis of the heatable device approximately coincides with a focal line of the third reflective surface. In such an embodiment, the heatable device is normally located inside the recess formed by the third reflective surface.

There are various ways of expressing the preferred geometries of the first and the third reflective surfaces.

For the first reflective surface, it is for example beneficial to have a relatively high focal length as it means a more planar reflective surface, which results in higher reflectance due to small incident angles and lower costs due to a smaller reflective surface. Accordingly, the parabola width to focal length ratio of the first reflective surface may in one embodiment be between 2:1 and 2.6:1, such as between 2.1:1 and 2.5:1. Another way of expressing the "flatness" of the first reflective surface is to use the parabola depth to focal length ratio, which for example may be between 1:2 and 1:4, such as between 1:2.5 and 1:3.5, such as between 1:2.8 and 1:3.2.

It is generally beneficial to keep the width of the parabola of the third reflective surface as small as possible to reduce the volume of the recess and thereby save on material and to obtain small incident angles on the heatable device, which results in better absorption by the heatable device.

Accordingly, the parabola width to focal length ratio of the third reflective surface may be between 4:1 and 6:1, such as between 4.4:1 and 50.4:1, such as between 40.6:1 and 50.2:1.

The purpose of the first reflective surface is to collect direct sunlight and it is therefore much bigger than the third reflective surface. Accordingly, the parabola width of the first reflective surface may be between 4 and 7 times, such as between 5 and 7 times, parabola width of the third reflective surface. The focal length of the first reflective surface may for example be at least 5 times, such as at least 8 times, such as 8-14 times, such as 9-13 times, such as 10-12 times, the focal length of the third reflective surface.

To avoid deviating too much from the industry standard for solar troughs, the parabola width of the first reflective surface may be 4-8 m, such as 5-7 m, such as 5.5-6.5 m. The length of the device of the third aspect (and thus the length of the first, second and third reflective surfaces) may for example be 4-6 m, such as 4.5-5.5 m.

In one embodiment, the second reflective surface divides the radiation into three different beams of which one is reflected directly to the heatable device and two are reflected to the heatable device via the third reflective surface. In another embodiment, the second reflective surface divides the radiation into at least four different beams of which at least two are reflected directly to the heatable device and at least two are reflected to the heatable device via the third reflective surface.

In the embodiments with 3 or more beams, the incident radiation on the heatable device is distributed around the circumferential surface of the heatable device. Such distributed incident radiation provides for a uniform heating of the heatable device, which improves heat absorption. Non-uniform heating may result in that the heatable device curves and gets damaged.

It follows form the above that the heatable device may be arranged in the recess defined by the third reflective surface. The recess may for example be provided with a cover such that the heatable reactor in the recess is protected. The cover is preferably composed of a material with high transmittance such as high-transmittance glass. It is particularly preferred that the transmittance of longer wavelengths, such as 900-2500 nm, is high when the second reflective surface is semi-reflective (see below).

The second reflective surface may for example be semi-reflective such that it can reflect longer wavelengths (e.g. 900-2500 nm) to the heatable device and/or third reflective surface and transmit shorter wavelengths comprising visible light to a photovoltaic cell arrangement. The semi-reflective surface may for example be obtained by a semi-reflective surface texture or a semi-reflective layer, such as a dichromatic layer.

The first, second and third reflective surfaces may be arranged to collectively turn such that the first reflective surface tracks the sun over the day. In such an embodiment, the first, second and third reflective surfaces may be arranged to turn around the axis of the heatable device, while the heatable device is fixed and not turning.

In one embodiment of the third aspect, the device comprises the photovoltaic cell arrangement of the fourth aspect described below. In such an embodiment, the second reflective surface is the semi-reflective surface of the fourth aspect.

As a fourth aspect of the present invention, there is provided a semi-reflective photovoltaic cell arrangement comprising a plurality of non-overlapping photovoltaic cells, wherein a concave lens or lens portion having a semi-reflective surface is arranged on a first side of each photovoltaic cell such that radiation in a first wavelength range is concentrated to the photovoltaic cell and radiation of a second wavelength range is reflected and a second side of each photovoltaic cells is connected to a cooling arrangement.

In one embodiment, the semi-reflective surface is obtained by a semi-reflective surface texture or a semi-reflective layer, such as a dichromatic layer. Such a texture or layer is known to the skilled person.

In one embodiment of the fourth aspect, the lenses are formed by casting a lens material, such as siloxane or glass. The refractive index of the lens material is preferably between 1.3 and 1.6, such as between 1.4 and 1.6. Such a casting operation may also fix the positions of the photovoltaic cells. The lenses may be curved in two dimensions and straight in a third dimension, e.g. forming elongated ridges. Such a 2D lens may cover a plurality of photovoltaic arranged side by side in a row. In one embodiment of the fourth aspect, the arrangement comprises a plurality of parallel 2D lenses. Each of the parallel 2D lenses may cover a row of photovoltaic cells.

In one embodiment of the fourth aspect, the lens comprises a convex top surface, a bottom surface facing the photovoltaic cell(s) and two opposed side surfaces reaching from the bottom surface to the top surface. The side surfaces may be reflective such that radiation transmitted through the top surface may be reflected by the side surfaces to the photovoltaic cell(s) under the bottom surface. In one embodiment, the side surfaces are leaning outwardly. For example, the plane of a leaning side surface may form an angle of 4-45°, such as 5-30°, with respect to the normal of the plane of the photovoltaic cell(s).

In one embodiment of the fourth aspect, the radiation in the first wavelength range comprises visible light. In one embodiment, the first wavelength range comprises 400-700 nm. It may also comprise 400-800 nm or 400-900 nm. As understood by the skilled person, a broader first wavelength range means that a larger portion of the energy in the sunlight is converted to electricity. In one embodiment, the second wavelength range, which normally is intended for heating, comprises 1000-2000 nm, such as 900-2500 nm.

The cooling arrangement is arranged to cool the photovoltaic cells, which increases their efficiency. The cooling arrangement is preferably composed of metal. Further, the cooling arrangement may comprise channels for a cooling medium, such as water. The channels may for example have a circular or oval cross-section, which is beneficial if the cooling medium has a high pressure. The cooling arrangement may for example be extruded in one piece.

As a fifth aspect of the present invention, there is provided reactor comprising an outer circumferential selective surface. The selective surface absorbs radiation, which heats the reactor. In the fifth aspect, a pipe is provided inside the selective surface. Accordingly, the selective surface may be provided directly on the outer surface of the pipe. The pipe is designed to withstand high reaction temperatures (e.g. >800° C.) and pressures (e.g. >150 bar) inside the reactor. Further, the pipe is normally composed of a material having high heat conductivity. Thus, the pipe may be composed of a metal, such as Inconel.

Inside the pipe, there is provided an electrolyser layer. Accordingly, steam may be added to this layer of the reactor, which generates hydrogen and oxygen. The hydrolytic layer may for example comprise a plurality of electrolyser cells, such as solid oxide electrolyser cells (SOEC), such as zirconia SOEC.

Inside the electrolyser layer, there is provided a catalytic layer. The catalytic layer may comprise one or more $FeO_2$ and/or Cu/ZnO based catalysts, optionally with added oxides, such as $Ga_2O_3$, $Al_2O_3$, $ZrO_2$ and/or $Cr_2O_3$. $CO_2$ may be added to the catalytic layer. The catalytic layer normally catalyses the formation of the product in one or more steps. For example, carbon monoxide and oxygen may be formed from $CO_2$ in the catalytic layer. The carbon monoxide may then react with hydrogen from the electrolyser layer in the catalytic layer to form the product. The product may for example be methanol One or more reactions in the catalytic layer may be exothermic and thereby assist in the provision of heat to the electrolytic reaction in the electrolyser layer.

In an embodiment of the fifth aspect, the selective surface, the pipe and the electrolyser layer are concentric. Preferably, the selective surface, the pipe, the electrolyser layer and the catalytic layer are concentric. In one embodiment, the selective surface, the pipe, the electrolyser layer, the catalytic layer and the product channel are concentric.

It follows from the above that the reactor of the fifth aspect in one embodiment is shaped as a cylinder.

The reactor of the fifth aspect may further comprise an outer tube wall or membrane provided between the electrolyser layer and the catalytic layer. Accordingly, the outer tube wall or membrane separates the electrolyser layer from the catalytic layer. The outer tube wall or membrane is permeable to hydrogen produced in the electrolyser layer. Thus, the outer tube wall may be perforated.

Also, the reactor of the fifth aspect may further comprise an inner tube wall or membrane provided between the catalytic layer and the product channel. Accordingly, the inside of the inner tube wall or membrane defines the product channel. The inner tube wall or membrane is permeable to the product produced in the catalytic layer. Thus, the inner tube wall may be perforated.

In one embodiment, the reactor of the fifth aspect further comprises at least one oxygen valve for release of oxygen formed in the electrolyser layer. The at least one oxygen valve may also be arranged to release oxygen formed in the catalytic layer. Alternatively, at least one separate oxygen valve may be arranged for the release of oxygen formed in the catalytic layer.

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

FIG. 1 shows an embodiment of a system according to the second aspect of the present disclosure. $CO_2$ is provided in a $CO_2$ storage unit 101. Water is provided in a water storage unit 102. The water of the water storage 102 may be steam. $CO_2$ from the $CO_2$ storage unit 101 is supplied to a first 103 and a second 108 reactor via a $CO_2$ supply line 104. A pump (not shown) may be arranged on the $CO_2$ supply line 104 for pressurizing the $CO_2$. Water from the water storage unit 102 is supplied to the first 103 and the second reactor 108 via a water supply line 105. A pump 106 is arranged on the water supply line 105 for pressurizing the water/steam supplied to the first reactor 103. The reactors 103, 108 of the system are thus chemically connected in parallel.

In contrast, the reactors 103, 108 of the system are electrically connected in series 119. Further, they are electrically connected to a first 107 and a second 109 photovoltaic cell arrangement. Accordingly, electrical energy generated in the photovoltaic cell arrangements 107, 109 may be used to drive an electrolytic reaction in the reactor 103, 108. During operation, the photovoltaic cell arrangements 107, 109 are cooled using a cooling medium (not shown). The cooling medium may for example be water from the water storage unit 102, which water in such case is preheated. Alternatively, the cooling medium from the photovoltaic cell arrangements 107, 109 may be heat exchanged with the water in the water supply line 105 (not shown).

In the reactors 103, 108, which comprise electrolytic cells and catalyst(s), methanol is formed from water and $CO_2$. The product mixture obtained from the reactors comprises methanol as well as unreacted $CO_2$ and water. The product mixture may also comprise unreacted carbon monoxide (CO) and hydrogen gas ($H_2$), which may be obtained as intermediates in the reactions in the reactors 103, 108.

The reactors 103, 108 are heated with concentrated radiation from the sun (not shown in FIG. 1). Preferably, a first solar collector arrangement (not shown in FIG. 1) collects sunlight to the first reactor 103 and the first photovoltaic cell arrangement 107, while a second solar collector arrangement (not shown in FIG. 1) collects sunlight to the second reactor 108 and the second photovoltaic cell arrangement 109.

The first and the second collector arrangements are preferably arranged side by side, e.g. to efficiently utilize the land where the system is set up.

Event though FIG. 1 only shows two reactors, it is understood that a commercial plant will normally comprise a much higher number of reactors and associated solar collector arrangements and photovoltaic cell arrangements that are arranged side by side in rows.

The pressure in the reactors 103, 108 may be about 220 bar, which means that the product mixture has the same pressure. Downstream the reactors 103, 108, a water separator 110 for separation of water/steam from the product mixture may be arranged. A water recycling line 111 may route the separated water/steam back to the water storage unit 102.

The product mixture is routed (after the optional water separator) to a piston engine 112, which is connected to a generator 113. The overpressure of the product mixture is thus converted to electrical energy. The reactors 107, 109 are electrically connected to the generator 113 via a generator connection 120. Accordingly, the generator 113 provides an extra supply of electrical energy for the electrolytic reaction in the reactors 103, 108.

The expanded product mixture from the piston engine 112 is condensed in a condenser 114 arranged downstream the piston 112 engine such that liquid methanol is obtained.

The cooling medium used in the condenser may for example be water from the water storage unit 102, which water in such case is preheated. Alternatively, the cooling medium from the condenser 114 may be heat exchanged with the water in the water supply line 105 (not shown).

The condensed product mixture from the condenser 113 may be routed to a syngas separator 115 and $CO_2$ separator 116 arranged downstream the condenser for separation of syngas and $CO_2$, respectively. A syngas recycling line 117 may recycle the syngas to reactors 103, 108. The recycled syngas is optionally mixed with $CO_2$ from the $CO_2$ storage unit 101 and/or the water/steam from the water storage unit 102 before being supplied to the reactors 103, 108. A $CO_2$ recycling line 118 may route separated $CO_2$ from the $CO_2$ separator 116 to the $CO_2$ storage unit.

Figure 2:
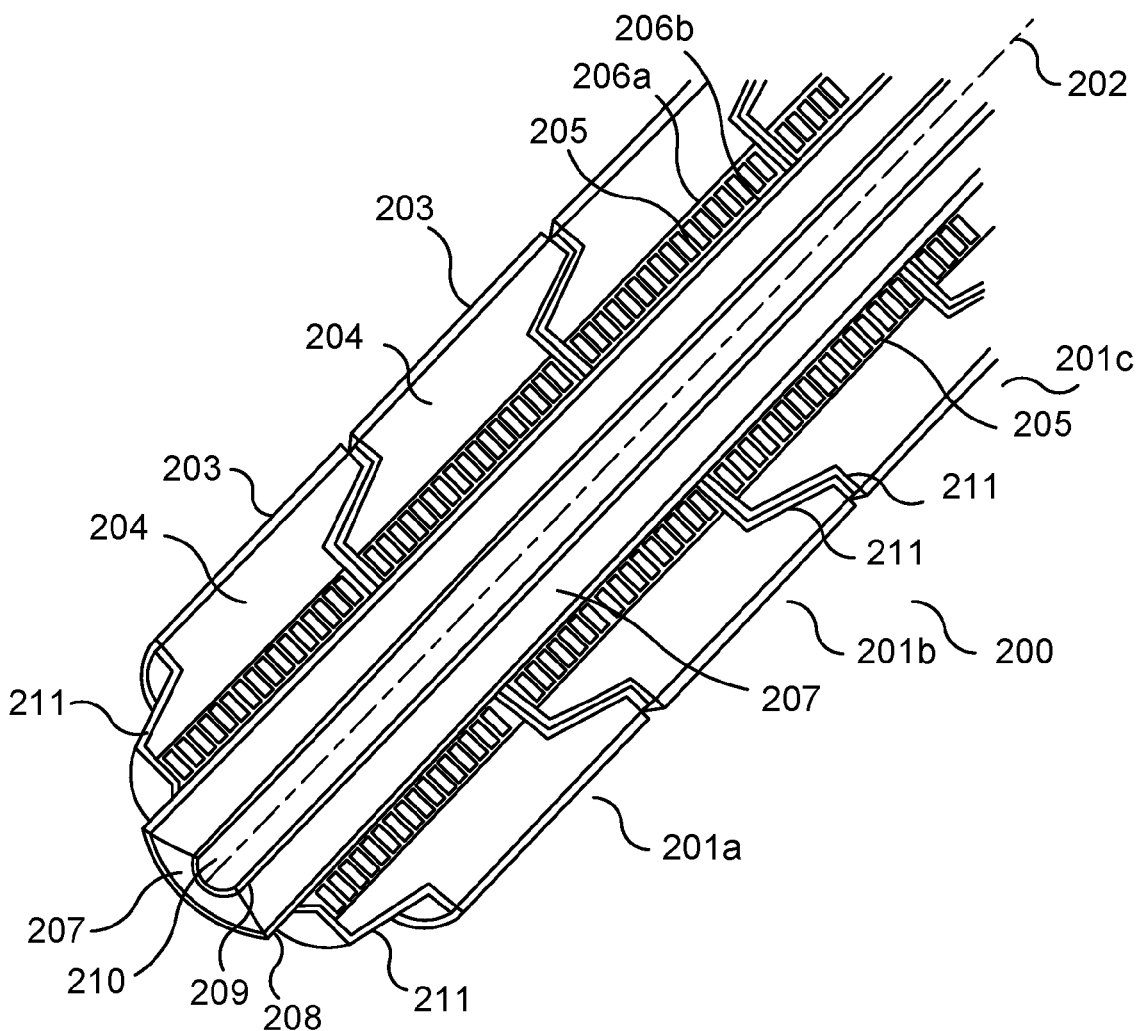
FIG. 2 is a longitudinal section of an embodiment of a reactor according to the fifth aspect of the present disclosure in perspective view.

FIG. 2 shows an embodiment of a generally cylindrical reactor 200 according to the fifth aspect of the present disclosure. The reactor 200 comprises a plurality of reactor segments 201a, 201b, 201c having a common a reactor axis 202. Each segment 201a, 201b, 201c comprises a circumferential selective surface 203 capable of efficiently absorbing radiation, while having a low thermal emittance.

The selective surface 203 is obtained by applying a layer of selective material, such as XXX or YYY, on the outer circumferential surface of a pipe 204. The material and thickness of the pipe 204 is selected such that a high reaction pressure, such as about 220 bar, can be maintained inside the pipe 204 at a high temperature. The pipe material may for example be a heat-resistant alloy, such as Inconel. Further, the heat conductivity of the pipe material is high so as to facilitate an efficient heat transfer from the selective surface 203 to the interior of the pipe 204. An electrolytic layer 205 comprising electrolytic cells is arranged inside the pipe 204 such that a small outer gap 206a is provided between the electrolytic cells and the inner surface of the pipe 204. Inside the electrolytic layer 205, there is provided a catalytic layer 207. An outer tube wall 208 separates the catalytic layer 207 from the electrolytic layer 205. A small inner gap 206b is provided between the outside of the outer tube wall 208 and the electrolytic cells. The outer tube wall 208 is designed to allow passage of hydrogen from the electrolytic layer 205 to the catalytic layer 207. An inner tube wall 209 separates the catalytic layer 207 from a central product channel 210. Accordingly, the inside of the inner tube wall 209 defines the central product channel 210. The inner tube wall 209 is designed to allow passage of methanol from the catalytic layer 207 to the central product channel 210.

Electrical connections 211 are provided at the ends of each segment 201a, 201b 201c such that electrical energy can be supplied to the electrolytic reaction in electrolytic layer 205.

Oxygen valves (not shown) may be provided in the pipe such that oxygen produced by the electrolysis in the electrolytic layer 205 can be released.

Figure 3:
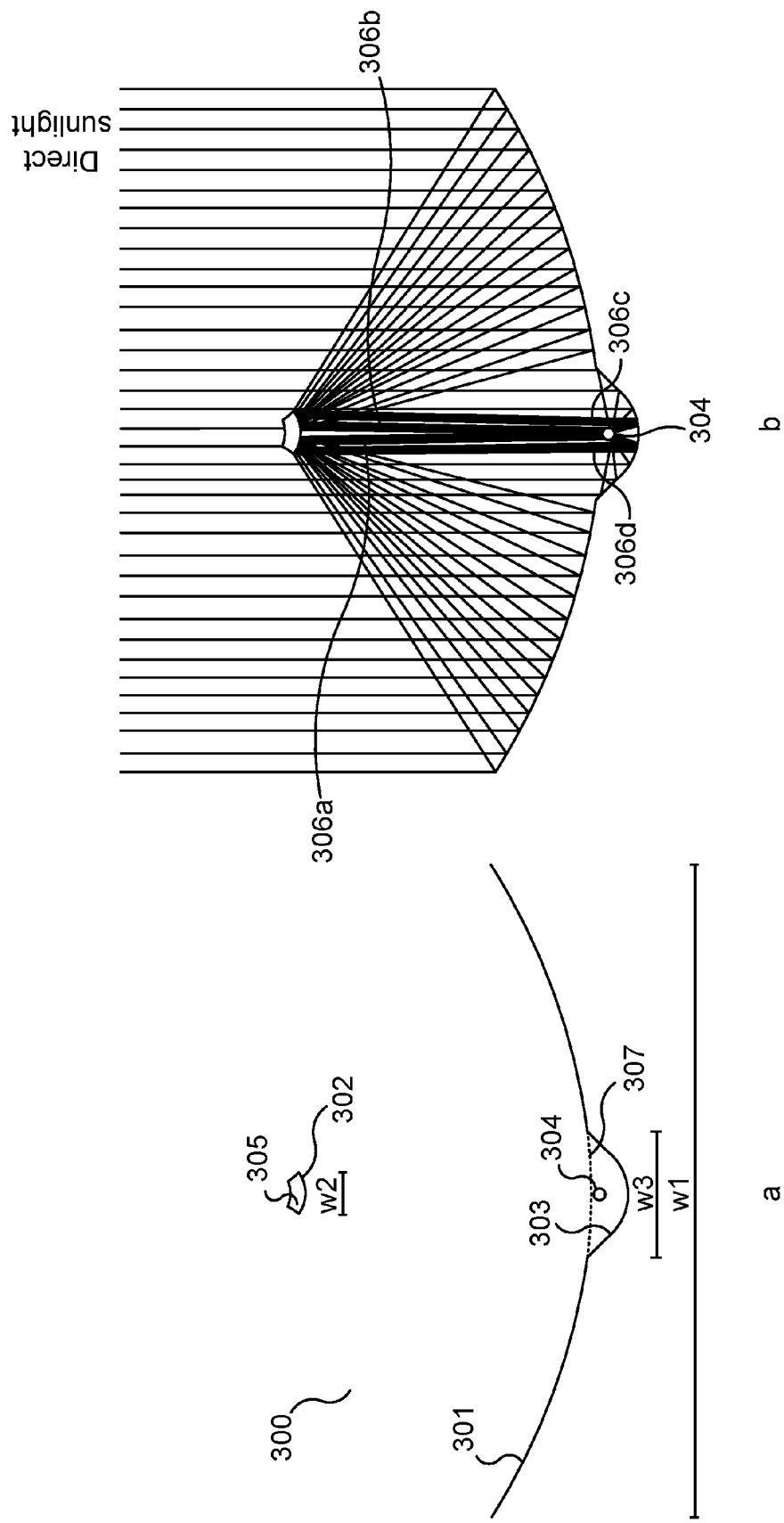
FIG. 3 illustrates a side view of an embodiment of a device for collection of sunlight according to the third aspect of the present disclosure.

FIG. 3 shows an embodiment of a solar collector 300 according to the third aspect of the present disclosure. The collector comprises a first reflecting surface 301 for primary reflection, a second reflecting surface 302 for secondary reflection and a third reflecting surface 303 for tertiary reflection and, to a smaller extent, primary reflection. The solar collector further comprises a cylindrical heatable reactor 304 having an absorptive selective surface.

The first reflective surface 301 is shaped as a parabolic trough, which means that the surface is straight in one dimension and curved as a parabola in the other two. The first reflective surface 301 is arranged to reflect and concentrate sunlight to the second reflective surface 302, which may be provided on a photovoltaic cell arrangement 305.

The second reflective surface 302 is arranged a short distance below the focal line of the first reflective surface 301. For example, the shortest distance between second reflective surface 302 and the focal line of the first reflective surface 301 the may be less than $\frac{1}{10}$ of the focal length of the parabola of the first reflective surface 301. It is beneficial to keep the width w2 of the second reflective surface 302 small to minimize shadowing. For example, the width w2 of the second reflective surface 302 may be less and $\frac{1}{8}$, such as less that $\frac{1}{10}$, of the width w1 of the first reflective surface 301.

The second reflective surface 302 may be semi-reflective such that longer wavelengths (e.g. 900-2500 nm) are reflected, while shorter wavelengths comprising the visual spectrum is converted to electrical energy in the photovoltaic cell arrangement 305.

The semi-reflective properties of the second reflective surface 302 may be obtained by a semi-reflective surface texture or a semi-reflective layer, such as a dichromatic layer.

The second reflective surface 302 is designed to create a plurality of radiation beams 306. In FIG. 3b, an embodiment of the second reflective surface 302 creating four different beams 306 is shown. Two direct beams 306a, 306b are directed directly to the heatable reactor 304, which is arranged below the second reflective surface 302. The two direct beams are thus hitting the upper half of the circumferential surface of the cylindrical reactor 304. Two indirect beams 306c, 306d are directed to the lower half of the circumferential surface of the cylindrical reactor 304 via the third reflective surface 303.

The third reflective surface 303 is provided as a recess in the first reflective surface 301. The third reflective surface 303 is also shaped as a parabolic trough. The placement of the cylindrical reactor 304 may be such that its central axis approximately coincides with the focal line of the third reflective surface 303.

The recess defined by the third reflective surface may be provided with a cover 307 composed of high transmittance material, such as high transmittance glass. In particularly preferred that the longer wavelengths reflected by the second reflective surface 302 are efficiently transmitted. The cover 307 encloses and protects the reactor 304.

The parabola width w1 of the first reflective surface 301 is thus much greater that the parabola width w3 of the third reflective surface 303. For example, it may be 5-7 times greater. Further, the optical power of the third reflective surface 303 is normally much greater than the optical power of the first reflective surface 301. Accordingly, the focal length of the first reflective surface 301 may for example be 10-11 times the focal length of the third reflective surface 303.

As seen in FIG. 3*b*, the third reflective surface 303 may also reflect some direct sunlight to the heatable reactor 304.

The parabola width w1 of the first reflective surface is normally approximately 6 meter, which is the standard width for parabolic troughs in the solar power industry. The length of the solar collector may be about 5 meter.

The position of the reactor 304 may be fixed, while the reflective surfaces 301, 302, 303 are arranged to track the sun by turning around the axis of the reactor 304, which is not turning. Such a construction allows for relatively uncomplicated coupling arrangements for supply of reactants and recovery of the product compared to a construction in which the reactor also turns during sun tracking.

Figure 4:
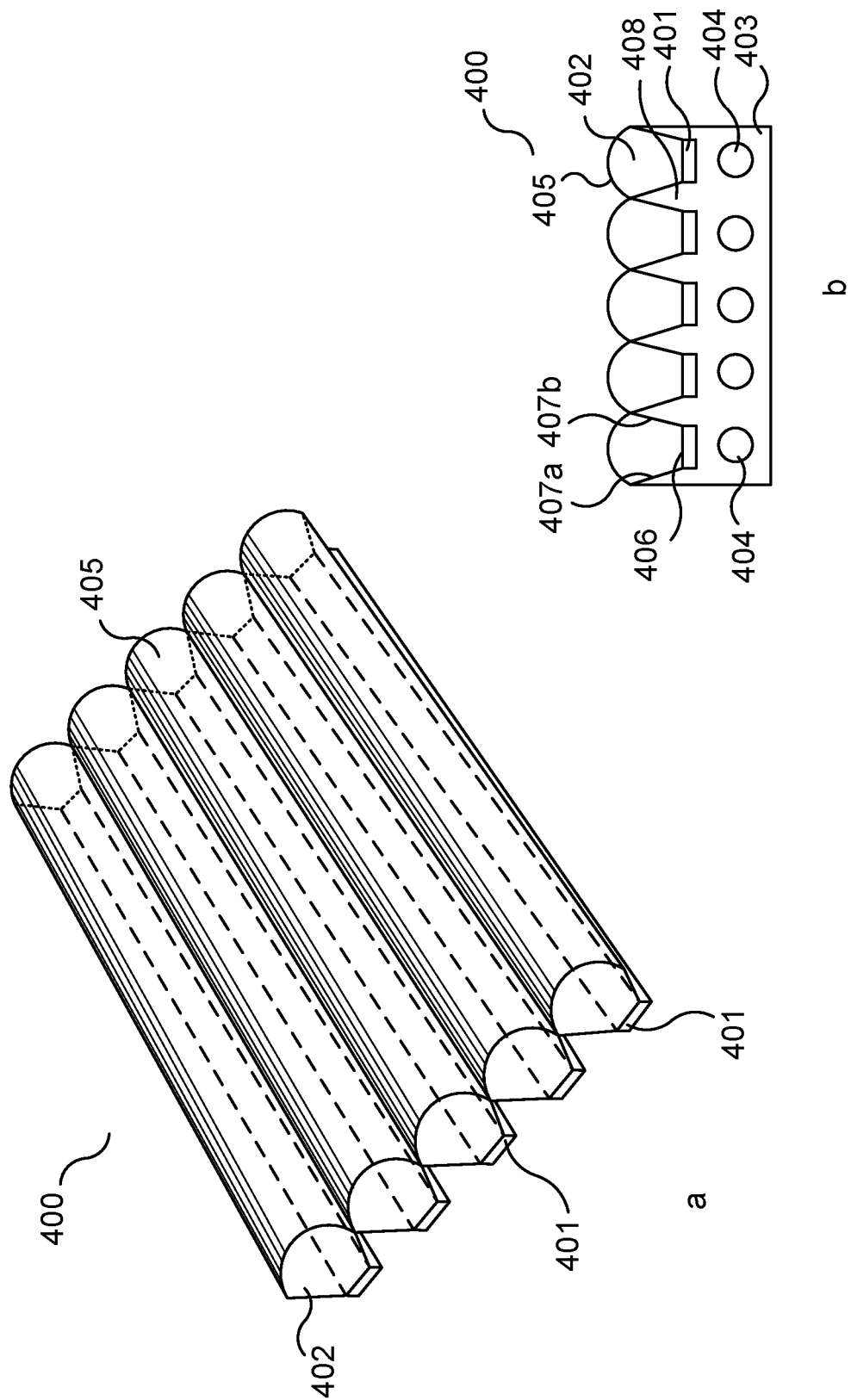
FIG. 4 illustrates an embodiment of a semi-reflective photovoltaic cell arrangement according to the fourth aspect of the present disclosure.

FIG. 4 shows an embodiment of a semi-reflective photovoltaic cell arrangement 400 according to the fourth aspect of the present disclosure.

The arrangement 400 comprises rows 401 of photovoltaic cells aligned side by side. The upper side of each row 401 is covered by an elongated 2D lens 402. Accordingly, each photovoltaic cell of the rows 401 is covered by a lens portion, which concentrates solar radiation to it. The underside of each row 401 is in thermal contact with a cooling arrangement 403 (only shown in FIG. 4*b*). The cooling arrangement 403 comprises channels 404 for a cooling medium, such as water. The cooling arrangement 403 is preferably composed of metal. The channels 404 may have a circular cross-section as shown in FIG. 4*b*.

The 2D lenses 402 have a semi-reflective surface 405 such that radiation in a first wavelength range is concentrated to the rows 401 of photovoltaic cells and radiation of a second wavelength range is reflected.

The semi-reflective top surface 405 of the 2D lenses 402 is convex. Each 2D lens 402 further comprises a bottom surface 406 facing the rows 401. In the embodiment of FIG. 4, each 2D lens 402 also comprises two opposed side surfaces 407*a*, 407*b* reaching from the bottom surface 406 to the top surface 405. The side surfaces 407*a*, 407*b*, which are leaning outwardly, are reflective such that radiation transmitted through the top surface 405 may be reflected by the side surfaces 407*a*, 407*b* to the photovoltaic cells of the rows 401. The cooling arrangement may comprise pointed extensions 408 contacting the side surfaces 407*a*, 407*b*. Such pointed extension 408 may also provide the reflectiveness of the side surfaces 407*a*, 407*b*, e.g. by being highly polished.

In one embodiment, the cooling arrangement 403 (preferably including the channels 404 and the pointed extensions 408) is extruded in one piece, which is cost efficient.

Figure 5:
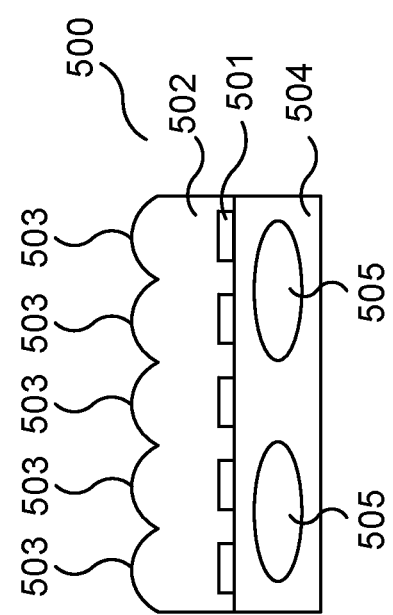
FIG. 5 illustrates a side view of another embodiment of a semi-reflective photovoltaic cell arrangement according to the fourth aspect of the present disclosure.

FIG. 5 shows another embodiment of a semi-reflective photovoltaic cell arrangement 500 according to the fourth aspect of the present disclosure.

As in FIG. 4, the arrangement 500 comprises rows 501 of photovoltaic cells aligned side by side. However, the rows 501 of FIG. 5 are embedded and fixed in a monolithic lens layer 502 formed by casting a lens material, such as siloxane. The upper side of the monolithic lens layer 502 is shaped to form a plurality of parallel 2D lens surfaces 503. Each 2D lens surface 503 forms a ridge in the monolithic lens layer 502 and cover one row 501 of photovoltaic cells. Accordingly, each photovoltaic cell of the rows 501 is covered by a lens portion, which concentrates solar radiation to it.

As in FIG. 4, the underside of each row 501 is in thermal contact with a cooling arrangement 504. The cooling arrangement 504 comprises channels 505 for a cooling medium, such as water. The cooling arrangement 503 is preferably composed of metal. The channels 505 of FIG. 5 have an oval cross-section. However, the cross-section may also have another shape, such as circular as in FIG. 4*b*.

The 2D lenses surfaces 503 are semi-reflective such that radiation in a first wavelength range is concentrated to the rows 501 of photovoltaic cells and radiation of a second wavelength range is reflected.

In one embodiment, the cooling arrangement 504 (including the channels 505) is extruded in one piece, which is cost-efficient.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method of producing a fuel product, comprising:
supplying electricity generated in a photovoltaic cell arrangement and a piston engine, respectively, to electrolytic and catalytic reactions that are heated by concentrated sunlight;
reacting carbon dioxide and water in the heated electrolytic and catalytic reactions to form a pressurized product; and
expanding the pressurized product in the piston engine to generate electricity and to obtain the fuel product.

2. The method of claim 1, wherein the piston engine is a hydraulic piston engine.

3. The method of claim 1, wherein at least one solar collector concentrates solar radiation to the photovoltaic cell arrangement for electricity generation and to the reactions for heating.

4. The method of claim 2, wherein the piston engine is a hydraulic piston engine-designed to operate at 5000-20000 rpm.

5. The method of claim 2, wherein the piston engine is a hydraulic piston engine-designed to operate at 10000-15000 rpm.

6. The method of claim 1, wherein the pressurized product is pressurized methanol.

* * * * *